(12) United States Patent
Thomas et al.

(10) Patent No.: US 11,049,015 B1
(45) Date of Patent: Jun. 29, 2021

(54) COMPUTER IMPLEMENTED METHOD FOR DETERMINING SURVEY SAMPLING PARAMETERS FOR ENVIRONMENTAL DNA DETECTION

(71) Applicant: Precision Biomonitoring Inc., Guelph (CA)

(72) Inventors: Mario Thomas, Cambridge (CA); Wenjuan Qi, Kitchener (CA)

(73) Assignee: PRECISION BIOMONITORING INC., Guelph (CA)

( * ) Notice: Subject to any disclaimer, the term of this patent is extended or adjusted under 35 U.S.C. 154(b) by 0 days.

(21) Appl. No.: 16/778,384

(22) Filed: Jan. 31, 2020

Related U.S. Application Data (60) Provisional application No. 62/799,375, filed on Jan. 31, 2019.

(51) Int. Cl.
   *G06N 3/08* (2006.01)
   *G01N 33/487* (2006.01)
   *G06K 9/62* (2006.01)

(52) U.S. Cl.
   CPC .......... *G06N 3/08* (2013.01); *G01N 33/48707* (2013.01); *G01N 33/48792* (2013.01); *G06K 9/6277* (2013.01)

(58) Field of Classification Search
   CPC .. G06N 3/08; G06K 9/6277; G01N 33/48707; G01N 33/48792
   See application file for complete search history.

(56) References Cited

U.S. PATENT DOCUMENTS 10,354,747 B1 * 7/2019 DePristo ............... G06T 7/0012

* cited by examiner

*Primary Examiner* — John W Lee
(74) *Attorney, Agent, or Firm* — Steven M. Greenberg, Esq.; Shutts & Bowen LLP (57) ABSTRACT

A computer implemented method for determining survey sampling parameters for environmental DNA (eDNA) detection comprises receiving a species selection identifying selected species and receiving environmental specifications for an environment to be tested for presence of the species. A sampling plan is generated using the environmental specifications and the species selection, and detectability prediction(s) are generated using the environmental specifications, the species selection and the current sampling plan to predict whether the selected species is detectable in the environment according to the current sampling plan. Where at least one respective selected species is undetectable according to the current sampling plan, the process iterates, with each subsequent iteration incorporating an increase in the total volume to be sampled, until either every respective selected species is detectable according to the then-current sampling plan or an iteration stop limit is reached. The sampling plan(s) and detection prediction(s) are generated using different algorithms.

30 Claims, 5 Drawing Sheets

COMPUTER IMPLEMENTED METHOD FOR DETERMINING SURVEY SAMPLING PARAMETERS FOR ENVIRONMENTAL DNA DETECTION

CROSS-REFERENCE TO RELATED APPLICATION

This application claims priority to United States Provisional Application No. 62/799,375 filed on Jan. 31, 2019.

BACKGROUND

Environmental DNA (eDNA) is DNA that is shed from an organism (macro or micro) into the environment and can be detected in cellular or extracellular forms. Detection of eDNA, or other nucleic acid (e.g. RNA), is a means to indirectly infer the presence of a species and is particularly useful to detect species that are difficult to sample using traditional methods, for non-invasively sampling critically endangered species, and for identifying obscure species. Sources of eDNA include cells, mucus, saliva, feces, urine, gametes, skin and hair.

An eDNA survey is an approach in which samples of soil, water, or even air are collected, and if the samples contain the DNA of the species of interest then conclusions can be drawn about the probability of this species being present in the location or not at the time of sampling. The eDNA approach has only been evolved recently and has slowly started to be used by environmental consultants and ecologists to monitor invasive and endangered aquatic species. eDNA can be used to identify many taxa including plants, mammals, fish, amphibians, fungi, virus and bacteria.

In one notable study, which is not admitted to be prior art, geneticist Neil Gemmell of the University of Otago, New Zealand, collected eDNA from Loch Ness in Scotland to see whether there might be evidence of the reputed "Loch Ness Monster". Although the study did not find any evidence of a Jurassic-era reptile like a plesiosaur, substantial quantities of eel DNA were identified, raising the tantalizing possibility that there is some truth to the "Nessie" rumors, and that the loch may harbor one or more unusually large eels that that account for the sightings (Science Focus, 5 Sep. 2019, https://www.sciencefocus.com/nature/loch-ness-monster-how-edna-helps-us-discover-what-lurks-beneath/).

Many factors were believed to affect the amount of eDNA present in an environmental sample, including, for example, the relative amount of target eDNA to the size of the environmental sample, size of the organism generating the eDNA, and the volume or intensity of eDNA secretion or shedding. The detection of eDNA is further complicated by the fact that it begins to degrade as soon as it is shed, and its presence is dependent on environmental conditions. Conditions such as exposure to UVB radiation, pH, heat, and the presence of microorganisms and endo- and exo-nucleases in the aquatic environment were generally expected to affect degradation of eDNA.

In addition to environmental factors, eDNA detection is further hampered by the presence of humic substances that may be co☐extracted with eDNA and inhibit the assay used to detect the eDNA, such as conventional PCR or quantitative PCR, thereby reducing the sensitivity and specificity of such assays.

Despite the challenges associated with eDNA detection, it has been an effective tool for identification of aquatic and semiaquatic species, and microbes in water sources. Detection of eDNA has largely been restricted to aquatic species, but it has also been used to a limited extent to determine the presence of terrestrial wildlife based on their eDNA in water sources.

One of the big constraints for adoption of eDNA methods by industry and regulators is the lack of statistical reliability in the survey designs, which are guestimates for the capture of heterogeneously distributed rare eDNA. Given the potential of eDNA for use to detect organisms of interest, e.g. species-at-risk or invasive alien species, it would be desirable to develop a robust method for designing consistent and reliable surveys for eDNA detection.

SUMMARY

Broadly speaking the present disclosure is directed to a computer-implemented method for determining survey sampling parameters for environmental DNA (eDNA) detection. A species selection identifying selected species and environmental specifications for an environment to be tested for presence of the species are received. A sampling plan is generated using the environmental specifications and the species selection, and detectability prediction(s) are generated using the environmental specifications, the species selection and the current sampling plan to predict whether the selected species is detectable in the environment according to the current sampling plan. Where at least one respective selected species is undetectable according to the current sampling plan, the process iterates, with each subsequent iteration incorporating an increase in the total volume to be sampled, until either every respective selected species is detectable according to the then-current sampling plan or an iteration stop limit is reached. The sampling plan(s) and detection prediction(s) are generated using different algorithms.

In one aspect, a computer implemented method for determining survey sampling parameters for environmental DNA (eDNA) detection comprises (a) receiving a species selection identifying at least one selected species, (b) receiving environmental specifications for an environment to be tested for presence of the at least one species, (c) receiving a current sampling plan, wherein the current sampling plan is generated using the environmental specifications and the species selection and comprises total volume to be sampled, total number of samples, volume per sample, and sample locations, (d) receiving, for each of the selected species, a respective detectability prediction as to whether the respective selected species is detectable in the environment according to the current sampling plan, wherein the respective detectability prediction is generated using the environmental specifications, the species selection and the current sampling plan, (e) testing according to each respective detectability prediction, whether at least one respective selected species is undetectable according to the current sampling plan, (f) where, according to each respective detectability prediction, at least one respective selected species is undetectable according to the current sampling plan, iterating through step (c), step (d) and step (e), wherein each subsequent iteration of step (c) incorporates an increase in the total volume to be sampled, until the earlier of (I) according to each respective detectability prediction, every respective selected species is detectable according to the current sampling plan, or (II) an iteration stop limit is reached, and (g) upon completion of step (e)(I), setting the then-current sampling plan as a final sampling plan. The respective detectability prediction as to whether the respective selected species is detectable in the environment according to the current sampling plan is generated using a detection prediction algorithm set, the current sampling plan is generated using a survey design algorithm set, and the detection prediction algorithm set is different from the survey design algorithm set.

In some embodiments, the method further comprises, before using the environmental specifications and the species selection to generate a first current sampling plan, providing the environmental specifications and the species selection to a filter, wherein the method terminates responsive to a determination by the filter that every selected species is undetectable in the environment. For a particular one of the selected species, the filter may determines that the selected species is undetectable in the environment because the selected species cannot be naturally present in the environment.

In some embodiments, the iteration stop limit is one of a volume limit and a number of iterations.

In some embodiments, for a particular one of the selected species, the respective detectability prediction indicates that the respective species is undetectable according to the current sampling plan because the particular one of the species, if present in the environment, cannot be detected according to the current sampling plan. In some embodiments, for a particular one of the selected species, the respective detectability prediction indicates that the respective species is undetectable according to the current sampling plan because the particular one of the species cannot be naturally present in the environment.

In some embodiments, the environmental specifications may comprise site type, study site surface area, study site perimeter, survey month, flow rate, water pH, water conductivity, water temperature, dissolved oxygen, turbidity, total suspended solids, total dissolved solids, presence of inhibitors, and eDNA detection results obtained from past surveys under given site data. Each respective detectability prediction is derived from the environmental specifications and may be further derived from a species-specific dataset for that species, the species-specific dataset comprising, for each species, the class of life, the species itself, average biomass, habitat preference, diet type, preferred water depth range, preferred temperature, spawning period, and detection limit.

In particular embodiments, the at least one species is at least one aquatic species, the environment is an aquatic environment and the current sampling plan comprises filter pore size.

In some embodiments, the detection prediction algorithm set comprises at least two of Generalized Linear Model, Generalized Estimating Equation, Generalized Additive Model, Random Forest and Neural Network.

In some embodiments, for a given selected species, the detectability prediction indicates that that selected species is detectable according to the current sampling plan where at least one of the detection prediction algorithms indicates that that selected species is detectable according to the current sampling plan.

In other aspects, the present disclosure is directed to a data processing system adapted for determining survey sampling parameters for eDNA detection according to the above-described method, and to a computer program product for determining survey sampling parameters for eDNA detection according to the above-described method.

BRIEF DESCRIPTION OF THE DRAWINGS

These and other features will become more apparent from the following description in which reference is made to the appended drawings wherein.

DETAILED DESCRIPTION

Aspects of the present technology are described in the context of sampling to identify aquatic species in an aquatic environment, for purposes of illustration. The present technology is not limited to aquatic environments. It can be applied, for example, to determining survey sampling parameters for environmental DNA (eDNA) detection in soil or even air, with suitable modifications which will be apparent to one of skill in the art, now informed by the present disclosure, which describes a computer implemented method for determining survey sampling parameters for environmental DNA (eDNA) detection.

The ecology of a target species refers to one or more of life-history or developmental stage, habitat, diet, interactions with other species, spawning habits, ontogenetic migration, and seasonal cycles. Knowledge of all aspects of the ecology of a target species provides the basis for a reproducible robust method of detection in which Type 1 errors (false positives) and Type II errors (false negatives) are minimized. Determination of the preferred habitat and diet of a species is important in determining sample sites for detection. An understanding of the spawning habits (e.g. pre-spawning, spawning and post-spawning) and/or migration patterns of a target species at various developmental stages and at different times of the year may also be important in this regard. For example, many aquatic organisms migrate to deeper waters as they transition from the juvenile to adult developmental stage. Migratory patterns may also be dictated by climatic variables (e.g., onset of spawning migrations may be linked to water temperature, or the occurrence of a threshold number of 'warm' days) and seasonal cycles.

Initially, a sampling site or sites are selected for obtaining environmental water samples for detection of the target species. The selection of the sampling site may be based on the ecology of the target species, for example, preferred habitat such as aquatic or terrestrial, physical factors such as temperature, soil and light intensity, and biological factors such as food source and presence of predators. For example, one would usually not look for a great white shark in a small inland lake. Alternatively, it may be desirable to identify all species residing in an environment, for example in developing an environmental impact statement.

Examples of sampling sites from which environmental water samples may be obtained include a sea, bay, marsh, lake, river, rivulet, stream, canal, culvert, creek, pond, vernal pond, swamp or wetland. The properties of the environmental water at the selected site or sites that govern the distribution of environmental nucleic acid molecules (such as eDNA) are then determined, to the extent possible, for the purpose of inputting these variables in a software tool that implements the method. Such properties may include water quality, e.g. pH, conductivity, turbidity, salinity, temperature, total dissolved solids, dissolved oxygen levels, presence of chemicals such as nitrogen and phosphorus, presence of known PCR inhibitors (e.g. humic acids), type and level of plant life, microbial organisms, algae, insects, and higher lifeforms. The presently described illustrative embodiments may use a subset of these properties; additional properties may be incorporated. Hydrological characteristics may also be considered, e.g. precipitation, channel topology, streamflow, flow rate, substrate type, presence of anthropogenic modification, level of shading from solar ultraviolet light, and groundwater levels. The presently described illustrative embodiments use flow rate only, but other embodiments may further consider additional hydrological characteristics.

The time period or periods within which to obtain the environmental water sample for detection of the target species are also determined and entered as another co-variable in a software tool that implements the method.

Water sample filtering parameters, such as filtering material, filter pore size and filtering flow rate, are determined by the software tool based on relevant factors, including the selected location and properties of the environmental water. The presently described illustrative embodiments determine only pore size, but other embodiments may further determine other water filtering parameters. Filters suitable for use in the present method include, but are not limited to, cellulose filters such as nitrocellulose filters and nitrocellulose mixed ester filters (NME—nitrocellulose and cellulose acetate). Suitable pore size is determined based on the expected load of suspended material in the sample. The smaller the pore size, the greater the amount of material that will concentrate on the filter and the greater the amount of eDNA that will be collected. However, the use of smaller pore sizes may result in clogging of the filter and undesirable collection of PCR inhibitors on the filter. Increasing the pore size (maximum of 10 micrometers) will help to prevent collection of PCR inhibitors, but will potentially result in loss of eDNA through the filter pores. To compensate for this potential loss of eDNA, larger sample sizes may be used to increase the amount of captured eDNA. Where larger pore-sized filters are desirable due to the sediment load of the sample, filter material that can bind DNA as the water sample is passed through the filter may be used to prevent or reduce loss of eDNA through the filter. For example, nitrocellulose mixed ester filters can bind some free DNA making these filters suitable for use when large pore-sized filtering is conducted. Larger pore sizes also permit the use of a higher flow rate, increasing expediency of the water sampling process. Generally, preferred filter pore size is between 0.5 to 10 microns (e.g. 0.5, 0.65, 0.8, 1.0, 3.0, 5.0, 8.0 and 10.0 microns), and preferred filtering flow rate is between 0.1 and 1.5 L/min.

The computer-implemented method can also determine the number, location and volume of environmental water samples to obtain.

The use of a computer implemented method for predicting whether DNA of the target species can be detected, and if so, automatically developing survey sampling parameters for eDNA detection, advantageously eliminates guesswork and reduces possible sources of error. Additionally, this approach can provide statistical robustness to allow an absence of detection to support an inference of absence of the target species while avoiding unnecessary costs associated with surveys that are more extensive than necessary.

The computer-implemented method described herein provides a tool to develop customized eDNA survey designs that have high statistical accuracy. The computer-implemented method provides a sampling strategy to obtain a high probability of detection of the target eDNA, if present, by determining the appropriate locations, sampling depth, water volumes, number of samples and filter pore size. Significant co-variables are used to build statistical and machine-learning based models to predict eDNA detection/non-detection and total volume of water to collect and filter using both model-based methods and machine learning techniques, drawing on a database of biological and ecological information from past survey datasets. Again, while the present disclosure describes applications to aquatic species in an aquatic environment, it will be understood that the present technology is not limited to aquatic environments, and can be applied, for example, to determining survey sampling parameters for environmental DNA (eDNA) detection in soil or even air.

According to an aspect of the present disclosure, there is provided a computer implemented method for determining survey sampling parameters for environmental DNA (eDNA) detection.

Figure 1:
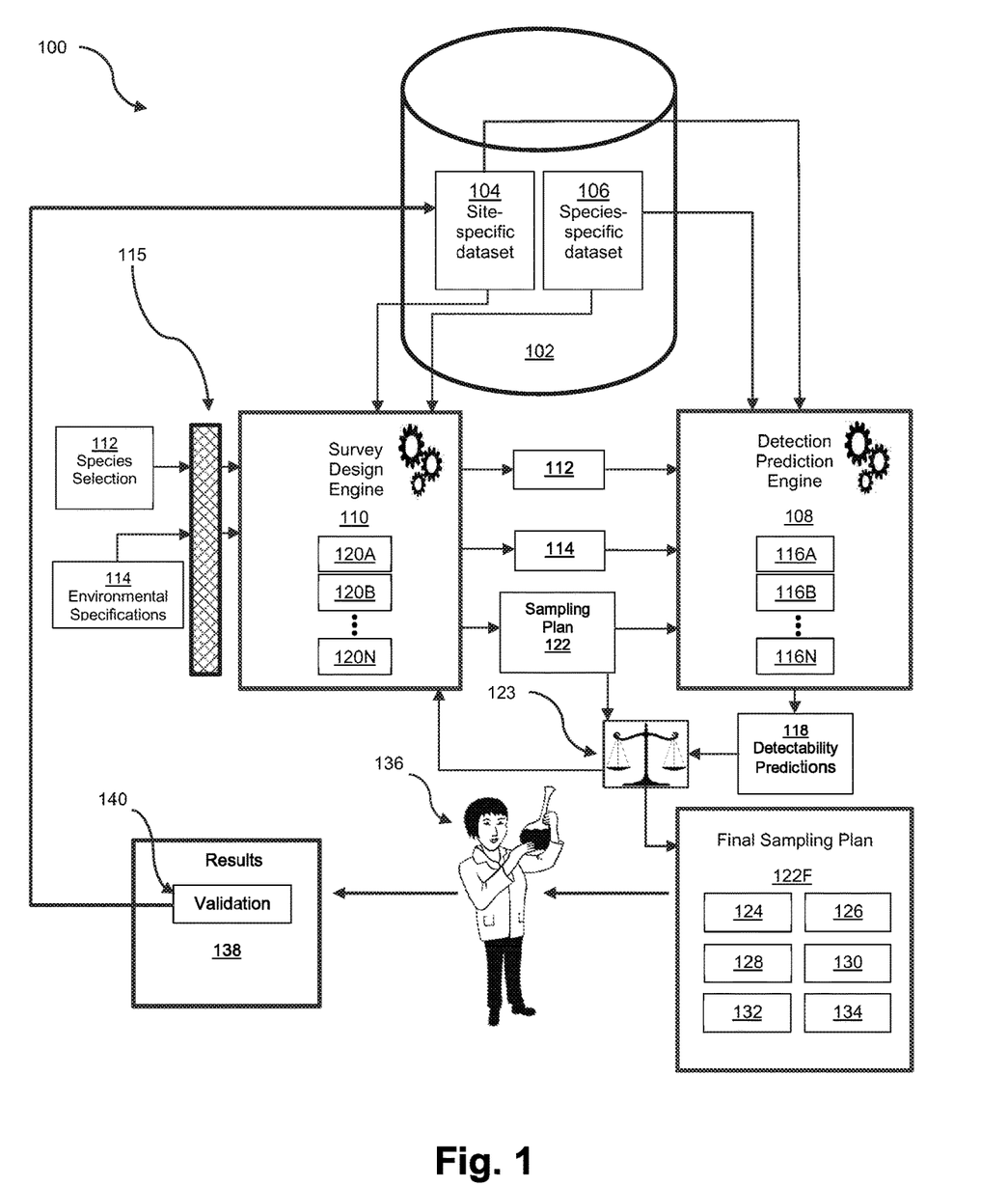
FIG. 1 is pictorial illustration of a process for determining survey sampling parameters for environmental DNA (eDNA) detection.

FIG. 1 is a pictorial illustration of a process 100 for determining survey sampling parameters for environmental DNA (eDNA) detection. A data store 102 includes a site-specific dataset 104 and a species-specific dataset 106. Although a single data store 102 is shown for simplicity of illustration, there may be more than one data store. For example, the site-specific dataset 104 and the species-specific dataset 106 may inhabit physically and/or logically separate data stores. The site-specific dataset 104 comprises historical values for certain variables relating to the design and results of actual previous surveys, and the species-specific dataset 106 comprises values for species-specific variables obtained from sources other than previous surveys, for example from scientific literature.

Examples of variables that may be stored in the site-specific dataset 104 for an aquatic environment include, but are not limited to, site type (e.g. lake, pond, river, wetland, marine), study site surface area (e.g. square feet, m$^2$), study site perimeter (e.g. feet, meters), survey month (e.g. January, February, etc.), flow rate (e.g. m/s for a river; may be zero for lake, pond, etc.), water pH, water conductivity, water salinity, water temperature, dissolved oxygen, turbidity, total suspended solids, total dissolved solids, solar UV exposure, presence of inhibitors (chemicals such as organic acids that may inhibit eDNA detection), phosphate level and nitrate level. The survey month variable will account for migration patterns. The site-specific dataset 104 must also contain eDNA detection results obtained from past surveys for different species under given site data. In one preferred embodiment, variables stored in the site-specific dataset 104 consist of site type, study site surface area, study site perimeter, survey month, flow rate, water pH, water conductivity, water temperature, dissolved oxygen, turbidity, total suspended solids, total dissolved solids, and presence of inhibitors, in addition to the eDNA detection results from past surveys. The fact that water salinity did not affect the outcome of the analysis was a surprising and unexpected result.

The variables stored in the species-specific dataset 106 are related to specific species of life. Examples of variables that may be stored in the species-specific dataset 106 include, but are not limited to, for each species, the class of life (e.g. mammal, bird, reptile), the species itself (e.g. *Canis lupus familiaris* for a domestic dog, or *Acipenser transmontanus* for a white sturgeon), the DNA shedding rate, average biomass, habitat preference, diet type, preferred water depth range, preferred temperature, spawning period, and detection limit. The detection limit is the sensitivity of the DNA test measured in copy numbers, which depends on the length of the DNA sequence needed to uniquely identify the species. In one preferred embodiment, the variables stored in the species-specific dataset 106 consist of, for each species, the class of life, the species itself, average biomass, habitat preference, diet type, preferred water depth range, preferred temperature, spawning period, and detection limit. The fact that the DNA shedding rate was not relevant was a surprising and unexpected result. The species-specific dataset 106 may be implemented, for example, as a MySQL® database.

The process 100 further comprises a detection prediction engine 108 and a survey design engine 110. In the illustrated embodiment, the detection prediction engine 108 and the survey design engine 110 are executed in R code, although other suitable programming languages may also be used.

The detection prediction engine 108 comprises a set of one or more detection prediction algorithms. Preferably, the set of detection prediction algorithms comprises a plurality of detection prediction algorithms 116A, 116B . . . 116N. In a current embodiment, there are five detection prediction algorithms 116A, 116B . . . 116N as described further below. The detection prediction algorithm(s) 116A, 116B . . . 116N may draw on data from the site-specific dataset 104 and/or the species-specific dataset 106, or the relevant data may be explicitly or implicitly integrated into the detection prediction algorithm(s) 116A, 116B . . . 116N, for example from training during a machine learning process. The term "algorithm" as used herein is to be interpreted broadly, and includes, for example and without limitation, programmed procedural algorithms, models, trained neural networks and other results of machine learning applications.

The survey design engine 110 comprises a set of one or more survey design algorithms. Preferably, the set of survey design algorithms is a plurality of survey design algorithms 120A, 120B . . . 120N. The survey design algorithm(s) 120A, 120B . . . 120N may draw on data from the site-specific dataset 104 and/or the species-specific dataset 106, or the relevant data may be integrated, explicitly or implicitly, into the survey design algorithm(s) 120A, 120B . . . 120N, for example from training during a machine learning process. As noted above, the term "algorithm" is to be interpreted broadly, and includes, for example and without limitation, programmed procedural algorithms, models, trained neural networks and other results of machine learning applications.

Importantly, and in fact critically to the present technology, the detection prediction algorithms 116A, 116B . . . 116N are different from the survey design algorithms 120A, 120B . . . 120N. Importantly, and in fact critically, the detection prediction algorithms 116A, 116B . . . 116N and the survey design algorithms 120A, 120B . . . 120N are not merely the same underlying equations with different coefficients, or the same machine learning models with different training/tuning. While there may be limited overlap, the set of detection prediction algorithms 116A, 116B . . . 116N does not contain the set of survey design algorithms 120A, 120B . . . 120N, nor does the set of survey design algorithms 120A, 120B . . . 120N contain the set of detection prediction algorithms 116A, 116B . . . 116N, even discounting differences in coefficients or training/tuning. The present process 100 is designed to use two distinct, different, independent engines, namely the detection prediction engine 108 and the survey design engine 110, which are developed and implemented separately and which rely on different internal algorithms, and wherein the sampling plans 122 generated by the survey design engine 110 are provided as input to the detection prediction engine 108.

The survey design engine 110 receives a species selection 112 identifying at least one aquatic species and environmental specifications 114 for an aquatic environment to be tested for presence of the identified aquatic species. The species selection 112 can be provided through a suitable user interface. For example, a user could type the scientific name (e.g. "*Acipenser transmontanus*") or the common name (e.g. "white sturgeon"); common names could be checked against a look-up table to retrieve the scientific name. Alternatively, pull-down menus could be used, for example tiered pull-down menus. Thus, a first menu could list "fish", "birds", "mammals", "amphibians", "reptiles", "vegetation", "microorganism", and if "fish" is selected, a second pull-down menu could list types of fish, including, for example, "pike", "perch", "salmon", "sturgeon", etc. If "sturgeon" were to be selected, the next menu could list the types of sturgeon. The species selection 112 may specify more than one species. The environmental specifications 114 for the aquatic environment to be tested correspond to the variables stored in the site-specific dataset 104. Thus, the environmental specifications for an aquatic environment may include site type, study site surface area, study site perimeter, survey month, flow rate, water pH, water conductivity, water temperature, dissolved oxygen, turbidity, total suspended solids, total dissolved solids, solar UV exposure, presence of inhibitors, phosphate level and nitrate level. The environmental specifications 114 may be provided as set values, or as ranges.

Optionally, the process 100 may include a filter 115, which carries out preliminary tests to avoid futile processing by the survey design engine 110 and the detection prediction engine 108. In such embodiments, before being provided to the survey design engine 110, the environmental specifications 114 and the species selection 112 are provided to the filter 115. Where a particular species is identified by the filter 115 as undetectable in the environment, an alert may be provided. If the filter 115 determines that every selected species is undetectable in the environment, the process 100 may terminate before initiating the survey design engine 110. In preferred embodiments, the filter tests one or more of the environmental specifications 114 against certain known parameters for the species indicated in the species selection 112, and terminates the process if the filter 115 determines that every selected species is undetectable in the environment. For example, the filter 115 may provide a pre-defined window for some of the variables in the environmental specifications 114, and will determine that detection of the target species is impossible if a variable is outside of the window. Typically, the window will be species-specific, and the filter 115 determines that the selected species is undetectable in the environment because the selected species cannot be naturally present in the environment. Thus, arctic species of fish would have a different temperature window than tropical species of fish. Other simple heuristics may also be used.

The survey design engine 110 uses the species selection 112 and the environmental specifications 114 as inputs to the survey design algorithm(s) 120 to generate an initial sampling plan 122. The sampling plan 122 includes a total volume (e.g. of water) to be sampled 124, a total number of samples to be taken 126, a volume per sample 128, sample locations 130, and (for aquatic environments and air) filter pore size 132. The sample locations 130 may specify both a geographical location (e.g. latitude and longitude) and a depth. The initial sampling plan 122 is then passed to the detection prediction engine 108, along with the species selection 112 and environmental specifications 114. While FIG. 1 shows the species selection 112 and the environmental specifications 114 being passed directly from the survey design engine 110 to the detection prediction engine 108, this is merely for simplicity of illustration and is not intended to imply architectural constraints or limitations.

The detection prediction engine 108 uses the species selection 112, environmental specifications 114 and initial sampling plan 122 as inputs to the detection prediction algorithms 116A, 116B . . . 116N to generate, for each of the aquatic species, a respective detectability prediction 118 as to whether that aquatic species is detectable in the aquatic environment, assuming that it is present, using the initial sampling plan 122. The detectability prediction(s) 118 may be expressed as either positive (e.g. a "1") if the species is detectable or negative (e.g. a "0") if the species is not detectable according to the sampling plan 122. In a preferred embodiment, each of the detection prediction algorithms 116A, 116B . . . 116N generates an independent prediction as to whether there will be a positive detection, assuming the target species is present, based on the environmental specifications 114. For each species, as long as at least one of the detection prediction algorithms 116A, 116B . . . 116N generates a positive prediction, even if none of the others do so, then the overall detectability prediction 118 will be positive, whereas if all of the detection prediction algorithms 116A, 116B . . . 116N generate a negative prediction, the detectability prediction 118 will be negative. More particularly, the overall detectability prediction 118 will be positive even if different algorithms predict detectability for different species. For example, if one fish and one frog are the selected species, and only a first detection prediction algorithm 116A predicts detectability of the fish and only a second detection prediction algorithm 116B predicts detectability of the frog, all selected species would still be considered detectable. In other embodiments, the results of the detection prediction algorithms 116A, 116B . . . 116N may be combined (e.g. an average, weighted average or other combination), and the detectability prediction 118 may be expressed as a probability of detection.

The detection prediction engine 108 (or one of the detection prediction algorithms 116A, 116B . . . 116N) may determine that an aquatic species cannot be detected for a number of reasons. For example, the detection prediction engine 108 may determine that the particular one of the at least one aquatic species, if present in the aquatic environment, cannot be detected according to the current sampling plan (e.g. because the quantity of DNA would be below the statistical limit of detectability given the current sampling plan 112). Another example would be where the detection prediction engine 108 determines that the particular one of the at least one aquatic species cannot be naturally present in the aquatic environment. Preferably, simple cases of this type, such as where the species is too large (e.g. a white sturgeon in a small pond) or unsuited to survive (e.g. a tropical fish in an arctic environment) would be caught by the filter 115; a determination by the detection prediction engine 108 that a species cannot be naturally present will generally be based on more complex and less predictable multi-variate interactions.

A test engine 123 tests, according to each respective detectability prediction 118, whether at least one respective selected species is undetectable according to the initial sampling plan 122. While the test engine 123 is shown as a separate module in FIG. 1 for purposes of illustration, it may be integrated into the detection prediction engine 108 or the survey design engine 110.

If the test engine 123 determines that, according to each respective detectability prediction, every respective selected species is detectable according to the initial sampling plan 122, the initial sampling plan 122 is set as a final sampling plan 122F. However, if the test engine 123 determines that, according to each respective detectability prediction 118, at least one respective selected species is undetectable according to the initial sampling plan 122, then the survey design engine 110 and the detection prediction engine 108 will begin to iterate.

The survey design engine 110 will again use the species selection 112 and the environmental specifications 114 as inputs to the survey design algorithm(s) 120 to generate a new, current sampling plan 122, which incorporates an increase in the total volume 124 to be sampled. This increase may be a fixed stepwise increase (e.g. 1 liter per iteration), or a variable increase. Examples of variable increases in the total volume 124 to be sampled include, but are not limited to, functions of the number of prior iterations and, where the detectability prediction 118 is a probability, functions of the most recent prior detectability prediction 118 (e.g. a higher detectability prediction 118 may result in a smaller increase in the next iteration). Thus, in some embodiments, the most recent prior detectability prediction 118 may be an input to the survey design engine 110. The then-current sampling plan 122 is then passed to the detection prediction engine 108.

The detection prediction engine 108 uses the species selection 112, environmental specifications 114 and the current sampling plan 122 as inputs to the detection prediction algorithms 116A, 116B . . . 116N to generate, for each of the aquatic species, a respective detectability prediction 118 as to whether that aquatic species is detectable in the aquatic environment, assuming that it is present, using the current sampling plan 122. The test engine 123 then tests, according to each respective detectability prediction 118, whether at least one respective selected species is undetectable according to the current sampling plan 122.

Iteration of the survey design engine 110 and the detection prediction engine 108 continues until either a determination by the test engine 123 that, according to each respective detectability prediction 118, every respective selected species is detectable according to the current sampling plan 122, or an iteration stop limit is reached. The iteration stop limit may be, for example, a volume limit, or a number of iterations. A volume limit may be a variable limit, such as a percentage of the total volume of the aquatic environment to be tested, or an absolute limit. An absolute limit may be, for example, 1000 liters. Likewise, a limit set as a number of iterations may be fixed or variable. If the survey design engine 110 and the detection prediction engine 108 reach the iteration stop limit, the survey design engine 110 may still provide a final sampling plan 122, which may include an indication 134 of which of the species are expected to undetectable. Alternatively, the survey design engine 110 may report that it is unable to design a sampling plan that will assure detectability of all specified species, if present.

Where iteration of the survey design engine 110 and the detection prediction engine 108 results in a determination by the test engine 123 that, according to each respective detectability prediction 118, every respective selected species is detectable according to the current sampling plan 122, the then-current sampling plan is set as a final sampling plan 122F.

The final sampling plan 122F can then be carried out and the samples tested 136 and the results 138, which may include validations 140 of the detectability prediction(s) 118, can be used to update the site-specific dataset 104, which can then be used to update the detection prediction algorithm(s) 116 and the survey design algorithm(s) 120. Where data provided by users is to be added to the site-specific dataset 104, it may first be subjected to a screening test to ensure its suitability.

Some illustrative approaches for constructing the detection prediction engine 108 will now be described.

A list of potential variables was developed based on the main factors expected to influence successful detection of rare eDNA in the water. The list was developed by considering variability in these categories: species biology and ecology, limit of detection of the DNA of the target species, DNA degradation, extraction process, water filtering, materials, PCR inhibition and environmental, physico-chemical and temporal conditions of the target sampling site. An initial list of 27 independent variables to be considered in statistical models was developed:

1. Class of animals
2. Target species
3. DNA shedding rate
4. Average biomass
5. Habitat preference
6. Diet type
7. Preferred water depth range
8. Preferred temperature range
9. Spawning period (e.g. month(s) in which the species spawn, including migratory spawning)
10. Site type (lake, pond, river, wetland, marine)
11. Study site area
12. Study site perimeter
13. Survey month
14. Flow rate
15. Water pH
16. Conductivity
17. Salinity
18. Temperature
19. Dissolved oxygen
20. Turbidity
21. Total suspended solids
22. Total dissolved solids
23. UV
24. Presence of inhibitors
25. Phosphate level
26. Nitrate level
27. Test limit of detection A dataset was assembled, primarily raw sampling data from previous surveys. In order to limit the effect of multicollinearity between covariates, several variables were eliminated due to missing values, and only variables which have a variance inflation factor (VIF) of less than 5 were considered in final models. After this process, correlation between each pair of variables was checked, and this did not identify any suspicious correlation between covariates. The final model was based on a dataset containing 581 observations and 22 variables (in addition to eDNA detection results obtained from past surveys under given site data):

1. Class of animals
2. Target species
3. Average biomass
4. Habitat preference
5. Diet type
6. Preferred water depth range
7. Preferred temperature range
8. Spawning period (e.g. month(s) in which the species spawn, including migratory spawning)
9. Site type (lake, pond, river, and wetland, marine)
10. Study site area
11. Study site perimeter
12. Survey month
13. Flow rate
14. Water pH
15. Conductivity
16. Temperature
17. Dissolved oxygen
18. Turbidity
19. Total suspended solids
20. Total dissolved solids
21. Presence of inhibitors
22. Test limit of detection Since these independent variables have different units with various ranges, standardization and rescaling (to within a range between 0 and 1) were applied to improve consistency and ease of interpretation. Windows and discrete variables were created based on the explanatory variables. For example, preferred temperature range of the species and temperature range of the environment could be expressed as windows, and diet type could be expressed as a discrete variable, e.g. "0" for vegetarian, "1" for carnivore or omnivore. Instead of using existing variables, new variables are used to fit models in order to achieve better performance such as a higher likelihood function on the existing dataset. The statistical modelling process was performed over several months.

The first model tested was the Habitat Occupancy Model, which is commonly used in ecology. The Habitat Occupancy Model assumes a three level (layer) hierarchical logistic model. For the inner layer, PCR sample detection probability is regressed onto laboratory related factors such as Limit of Detection (LOD). For the middle layer, biological replicate detection probability is regressed onto environmental related factors such as pH and water temperature. For the top layer, final occupancy probability is regressed onto site related variables such as perimeter. Although the Habitat Occupancy Model allows for fitting of three-layer models, the method has many drawbacks: it uses Markov chain Monte Carlo (MCMC) to generate parameters, which is computationally inefficient, and assumes that each observation has to be independent of each other observation. If each species is considered to be one observation, this approach would exhaust the degrees of freedom and can introduce multicollinearity (since n<p here). However, combining multiple species together with repeated measurements within each species may result in dependent observations in the dataset. Therefore, other models were considered, which allow for repeated measurements.

One such model was the Autoregressive Occupancy Model. The model used STAN (a probabilistic programming language, written in C++) implemented in R (a programming language and environment for statistical computing) to perform statistical inference. The Autoregressive Occupancy Model did not perform any better than the traditional Habitat Occupancy Model because the Autoregressive Occupancy Model had too many false positives (overestimating probability of detection), and there was insufficient available geographical data (latitude and longitude coordinates within each sampling site) to use this spatial approach. Thus, simpler (fewer parameter) models were considered to model the association.

Since traditional logistic regression violates the independence assumption, Generalized Linear Mixed-Effect Model (GLMM) was used to fit the dataset. Penalized GLMM in L1 and L2 norm were also applied in order to perform model selection in Lasso model. It was found that Elastic Net performed the best among penalized regression models based on 5-fold, 10-fold and 20-fold cross-validation results. Elastic Net will typically perform better than solely fitting L1 or L2 norm as a penalty if correlation exists. However, for Penalized Mixed-effect Regression Models, substantial effort was invested to estimate parameters and find optimal tuning parameters. Model selection still depends on the validation set; a different validation set will yield different optimal tuning parameters. Expected prediction error in cross-validation based on tuning parameters with minimum mean squared error (MSE) was susceptible of further improvement, so semi-parametric regression models such as additive models were also investigated.

Machine learning based additive models, which do not need to assume parametric form between each pair of coefficient and explanatory variable, were tested. These additive models achieve very good results compared to other models. Without being limited by theory, it is believed that this is because machine learning based additive models can reduce the bias caused by model imperfection.

One class of models used is tree-based methods. The Random Forest method and decision tree were applied to the dataset. Random Forest gave the best result (95% prediction accuracy in test set) because this method can reduce the variance toward the minimum. The error coming from bias is mainly due to model imperfection and imperfection in the variables used; variables were included based on known correlation between success of detection and each of species-specific or site-specific factors. These variables are able to provide information to predict future detection results. Variance produced from the model is mainly due to the number of variables included; therefore, in some circumstances it may be advantageous to sacrifice dimensionality (increase bias) to achieve better overall prediction error.

From deep-learning methods, a Neural Network approach also achieved very good results. Here, only a low number of neurons and four hidden layers are used to fit the model, in consideration of computation costs. Increases were made one unit of neurons at a time, and then increasing hidden layers, to compare model performance in prediction error, stopping when the model had the best prediction error but can still converge.

Models that were considered included Generalized Linear Model, Generalized Estimating Equation, Generalized Additive Model, Linear/Quadratic discriminant analysis model, Random Forest, Neural Network, Gradient boosting, Adabag boosting, Smooth Binomial Model and Support Vector Machine. Since different models have their own assumptions and mechanisms, each model must be trained to determine which models best fit the dataset. Even though each model has different training protocols, the general procedure is the same: use the same method of k-fold cross-validation to generate an independent training dataset and a test dataset. If the model has tuning parameters (e.g. Random Forest and Neural Network), a validation dataset is also generated. Model parameters are estimated from the training dataset, and the model's performance is examined based on the test dataset. Generalized Linear Model, Generalized Estimating Equation and Generalized Additive Model used the method mentioned above. For Random Forest and Neural Network, these algorithm-based models require generating a validation set to obtain a set of optimal tuning parameters. Tuning parameters that can reduce loss function the most will be treated as optimal tuning parameters. These tuning parameters are used to test model performance on the test dataset. Therefore, model performance on training data can be quantitatively evaluated based on metrics, such as F1 score and prediction accuracy.

The percentage hold-out and k-fold cross-validation may be performed as follows, with reported prediction accuracy in different percentages of the training dataset and the test dataset split for five models. One method is to generate (randomly) 100 seeds, and use each seed to choose the training dataset and the test dataset based on the same percentage, and average the result (accuracy) over 100 seeds. This process is repeated for each percentage (70%, 75%, 80%, 85%, 90%, 95%, 99%). Another method is to use k-fold, leaving one-fold as the test dataset and using the rest of the data as the training dataset. The training dataset is used to fit the model and then the test dataset and the model are used to obtain a predicted response. Root mean square error was calculated for continuous response variables such as total volume, and for binary response variables, prediction accuracy based on one-fold was used. This process was repeated for each fold and the average was taken. This procedure was performed for 5-fold, 10-fold, 20-fold, 30-fold, 40-fold and 50-fold.

Five machine-learning models were validated using two best-practice validation methods: hold-out validation and k-fold cross-validation. The five machine-learning models that were trained and validated were Generalized Linear Model, Generalized Estimating Equation, Generalized Additive Model, Random Forest and Neural Network. These models may be used as the detection prediction algorithms 116A, 116B . . . 116N in the detection prediction engine 108. Accordingly, in a preferred embodiment, the detection prediction algorithms 116A, 116B . . . 116N are trained machine-learning models. In one preferred embodiment, the detection prediction algorithm set comprises at least two, preferably at least three, more preferably at least four and most preferably all five of Generalized Linear Model, Generalized Estimating Equation, Generalized Additive Model, Random Forest and Neural Network. These are merely examples, and not intended to be limiting. In some embodiments, the detection prediction algorithms 116A, 116B . . . 116N may be trained and tuned differently depending on the class of life (e.g. fish, amphibian, reptile, mammal, etc.). Thus, although the same detection prediction algorithms 116A, 116B . . . 116N would still be used for each class, the detection prediction algorithms 116A, 116B . . . 116N may have class-specific training and tuning.

The methodology for survey design, that is, for developing the survey design engine 110, will now be described in the context of an aquatic environment, for purposes of illustration and not limitation. The survey design engine 110 outputs a sampling plan 122 with five dimensions: total volume 124, total number of samples to be taken 126, volume per sample 128, sample locations 130, and filter pore size 132. Machine-learning models were constructed to predict these dimensions. While many species-specific variables are crucial in model fitting, these can be retrieved from the species-specific dataset 106 based on the species selection 112. For example, the species-specific "limit of detection", "spawning period", "survey depth range of species", "surviving temperature in range for species" and "diet type" are all relevant to model fitting, and can be retrieved from a suitably populated species-specific dataset 106. Among all variables, only site-specific variables (i.e. based on the location where the survey is to be done) require user inputs, namely environmental specifications 114, from users; the species-specific dataset 106 will be pre-populated.

A pore size model is built based on a training dataset that only contains successful positive detections. The covariates considered were "turbidity" and "survey temperature" In one currently preferred embodiment, "pore size" only has two sizes: either less than 1 or around 5 micrometers. A PCR-Inhibition model was built based on "pH" and "turbidity" to predict if "PCR inhibition" exists. In the next stage, a training dataset only containing successful detections was used to fit a volume model and predict total volume per site, assuming the target species can be detected. If the detectability prediction 118 for the target species was negative (e.g. "0"), this model operates as an iterative loop which increases by one unit of total volume at each iteration, ceasing the iteration when the detectability prediction 118 for the target species becomes positive (e.g. "1") or if a maximum number of iterations (e.g. 1000 iterations) or maximum volume (e.g. 50 liters) is reached. For each machine-learning model, the procedure described in the above paragraphs is used. Various models are considered, trained, tuned (if applicable), and tested. If the initial detectability prediction 118 for the target species is positive, the initially predicted volume is used. After this process, the model to predict volume per sample is fitted based on the volume per sample variable in the site-specific dataset. The number of biological replicates (number of samples) based on total volume and volume per sample can be calculated using a mathematical function. Location and depth are determined from data in the species-specific dataset 106, for example by use of a look-up table.

In one illustrative embodiment, the code for the detection prediction engine 108 and the survey design engine 110 is written in the R language and preliminary tests have shown satisfactory run time. If further refinement or enhancements are undertaken, it may be desirable to rewrite/translate the code into another language, for example Python or C++. These are merely examples and do not imply any limitation on languages that may be used.

Figure 2:
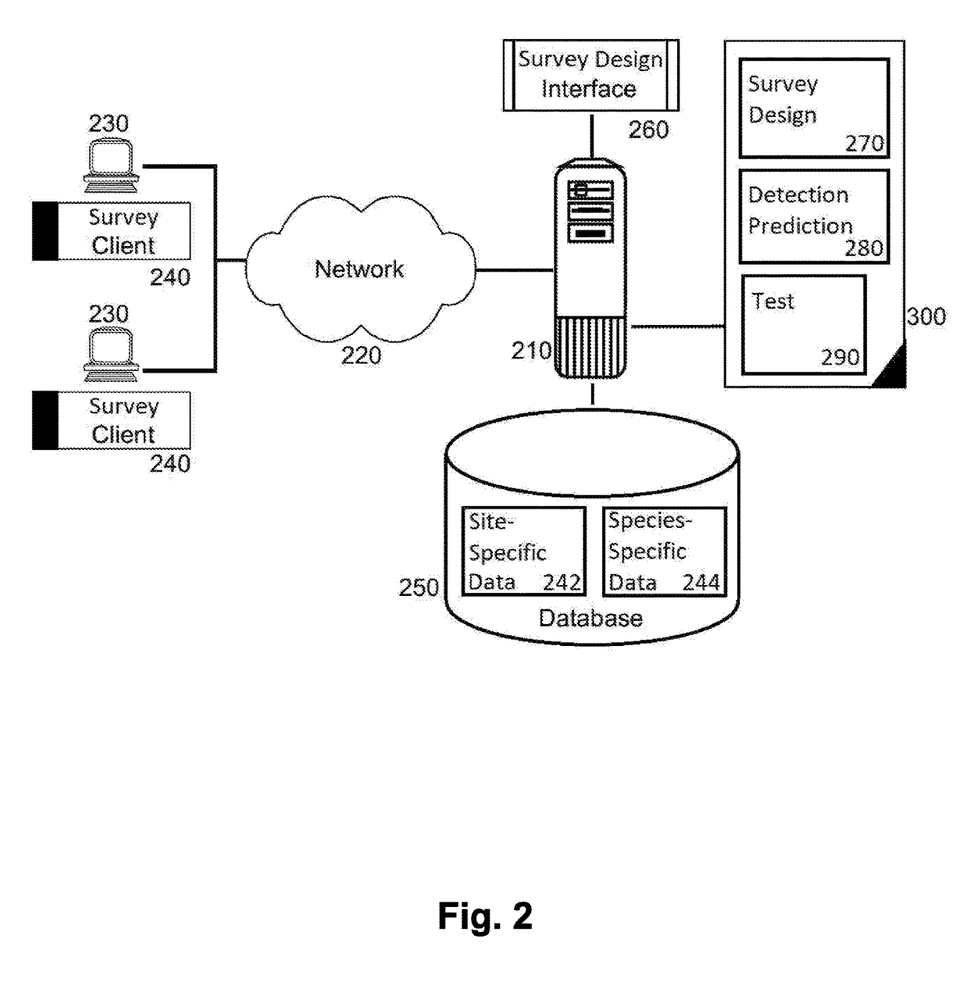
FIG. 2 is a schematic illustration of a data processing system configured for determining survey sampling parameters for environmental DNA (eDNA) detection.

The process described in connection with FIG. 1 can be implemented within a data processing system. In further illustration, FIG. 2 schematically shows a data processing system configured for determining survey sampling parameters for environmental DNA (eDNA) detection. The system includes a host computing platform 210 that includes one or more computers, each with memory and at least one processor. The system also includes a survey design interface 260 configured to receive species selections and environmental specifications over computer communications network 220 from survey clients 240 executing in respectively different computing devices 230, and to provide a final sampling plan in response. The system 200 further includes a database 250, which includes site-specific data 242 and species-specific data 244. Although a single database 250 is shown for simplicity of illustration, there may be more than one database.

Of importance, the system 200 includes a survey development iteration module 300, which includes a survey design sub-module 270, a detection prediction sub-module 280 and a test sub-module 290. The survey development iteration module 300 includes computer program instructions which when executed in the host computing platform 270, are enabled to receive from the survey clients 240, species selections and environmental specifications. The computer program instructions additionally are enabled upon execution to provide the environmental specifications and the species selection to the survey design engine 270, which returns a current sampling plan comprising a total volume to be sampled, a total number of samples, volume per sample and sample locations (as well as pore size for aquatic environments). The computer program instructions are further enabled upon execution to provide the environmental specifications, the species selection and the current sampling plan to the detection prediction sub-module 280, which returns, for each of the selected species, a respective detectability prediction as to whether the respective selected species is detectable in the environment according to the current sampling plan. The computer program instructions are further enabled upon execution to test, by the test sub-module 290, whether at least one selected species is undetectable according to the current sampling plan and if so, for so long as at least one selected species is undetectable according to the current sampling plan, to iterate through additional sampling plans, where each subsequent iteration of step incorporates an increase in the total volume to be sampled. The iteration continues until every respective selected species is detectable according to the current sampling plan or until an iteration stop limit is reached, after which the then-current sampling plan may be set as a final sampling plan.

The survey design interface 260 or the survey development iteration module 300 may incorporate filter logic, which carries out preliminary "filtering" tests on the species selections and environmental specifications to avoid futile processing by the survey development iteration module 300.

The detection prediction sub-module 280 uses a detection prediction algorithm set to use the environmental specifications, the species selection and the current sampling plan to generate, for each of the selected species, the respective detectability prediction as to whether the respective selected species is detectable in the environment according to the current sampling plan. The survey design sub-module 270 uses a survey design algorithm set to use the environmental specifications and the species selection to generate the current sampling plan. Importantly, and in fact critically, the detection prediction algorithm set is different from the survey design algorithm set.

Figure 3:
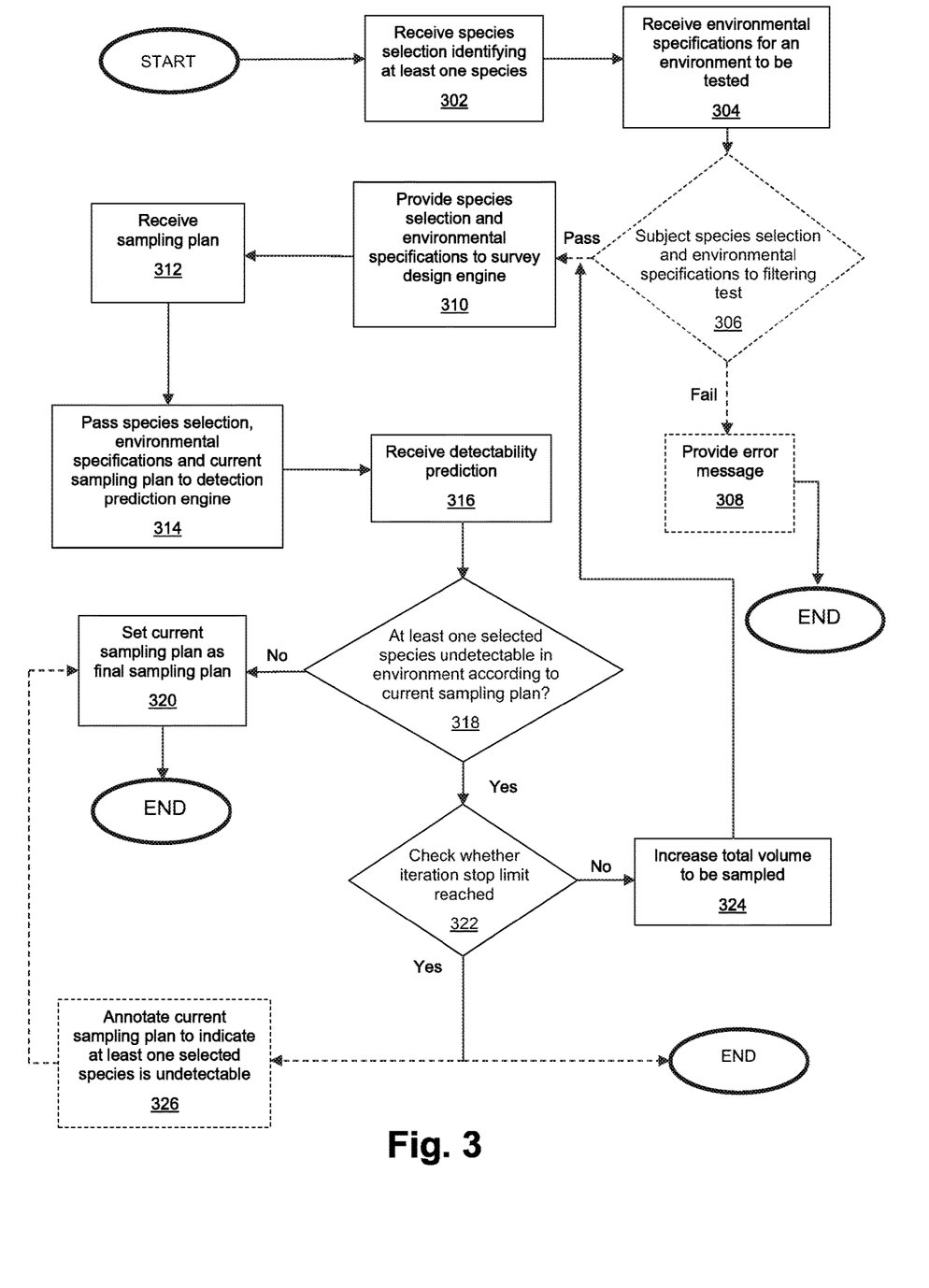
FIG. 3 is a flow chart illustrating a process for determining survey sampling parameters for determining environmental DNA (eDNA) detection.

In yet further illustration, reference is now made to FIG. 3, which shows an illustrative computer-implemented method for determining survey sampling parameters for environmental DNA (eDNA) detection.

At step 302, the method receives a species selection identifying at least one species and at step 304 the method receives environmental specifications for an environment to be tested for presence of the species. Steps 302 and 304 may be carried out in reverse order or substantially simultaneously.

Optionally, the species selection and the environmental specifications are subjected to a filtering test 306 to see whether some or all of the selected species may be undetectable in the environment, for example by applying species-specific windows or other heuristics to variables in the environmental specifications. If the filtering test 306 is failed, the method may provide an error message at step 308 and then end; if the filtering test 306 is passed, the method proceeds to step 310.

At step 310, the species selection and the environmental specifications are provided to a survey design engine, and at step 312 the method receives, from the survey design engine, a current sampling plan. The current sampling plan generated at the first iteration of step 312 is an initial sampling plan. The current sampling plan received at step 312 includes a total volume to be sampled, a total number of samples, a volume per sample, sample locations, and (for aquatic environments and air) filter pore size.

At step 314, the method passes the species selection, the environmental specifications and the current sampling plan to a detection prediction engine, and at step 316, the method receives from the detection prediction engine, for each of the selected species, a respective detectability prediction as to whether the respective selected species is detectable in the environment according to the current sampling plan.

At step 318, the method tests, according to each respective detectability prediction, whether at least one respective selected species is undetectable according to the current sampling plan. If the test determines that, according to each respective detectability prediction, every respective selected species is detectable according to the current sampling plan ("no" at step 318) the method proceeds to step 320 to set the then-current sampling plan as a final sampling plan and then ends. If the test determines that, according to each respective detectability prediction, at least one respective selected species is undetectable according to the current sampling plan ("yes" at step 318) the method proceeds to step 322.

At step 322, the method checks whether an iteration stop limit has been reached. If the iteration stop limit has not been reached ("no" at step 322), the method proceeds to step 324 to increase the total volume to be sampled, and then returns to step 310. If the iteration stop limit has been reached ("yes" at step 318), the method ends without marking the current sampling plan as a final sampling plan. Alternatively, if the iteration stop limit has been reached ("yes" at step 318), the method may proceed to optional step 326 to annotate the then-current sampling plan to indicate that at least one selected species is undetectable, and then to step 320 to set the then-current sampling plan, now annotated, as a final sampling plan.

As noted above, the detection prediction engine comprises a detection prediction algorithm set, the survey design engine comprises a survey design algorithm set, and the detection prediction algorithm set is different from the survey design algorithm set. The computer system(s) executing the detection prediction engine and the survey design engine may be different computer systems from the computer system that executes the method, or may be the same computer system.

As can be seen from the above description, the eDNA survey design systems and methodologies described herein represents significantly more than merely using categories to organize, store and transmit information and organizing information through mathematical correlations. The eDNA survey design systems and methodologies are in fact an improvement to the technology of eDNA collection, as they provide a robust method for designing consistent and reliable surveys for eDNA detection. They can also provide statistical robustness to allow an absence of detection to support an inference of absence of the target species while avoiding unnecessary costs associated with surveys that are more extensive than necessary. As such, the eDNA survey design systems and methods are confined to eDNA detection applications.

Aspects of the present technology may be embodied within a system, a method, a computer program product or any combination thereof. The computer program product may include a computer readable storage medium or media having computer readable program instructions thereon for causing a processor to carry out aspects of the present technology. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technology may be assembler instructions, instruction-set-architecture (ISA) instructions, machine instructions, machine dependent instructions, microcode, firmware instructions, state-setting data, or either source code or object code written in any combination of one or more programming languages, including an object oriented programming language or a conventional procedural programming language. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to implement aspects of the present technology.

Aspects of the present technology have been described above with reference to flowchart illustrations and/or block diagrams of methods, apparatus (systems) and computer program products according to various embodiments. In this regard, the flowchart and block diagrams in the Figures illustrate the architecture, functionality, and operation of possible implementations of systems, methods and computer program products according to various embodiments of the present technology. For instance, each block in the flowchart or block diagrams may represent a module, segment, or portion of instructions, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Some specific examples of the foregoing may have been noted above but any such noted examples are not necessarily the only such examples. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It also will be understood that each block of the flowchart illustrations and/or block diagrams, and combinations of blocks in the flowchart illustrations and/or block diagrams, can be implemented by computer program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, other programmable data processing apparatus, or other devices to function in a particular manner, such that the instructions stored in the computer readable storage medium produce an article of manufacture including instructions which implement aspects of the functions/acts specified in the flowchart and/or block diagram block or blocks. The computer readable program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 4:
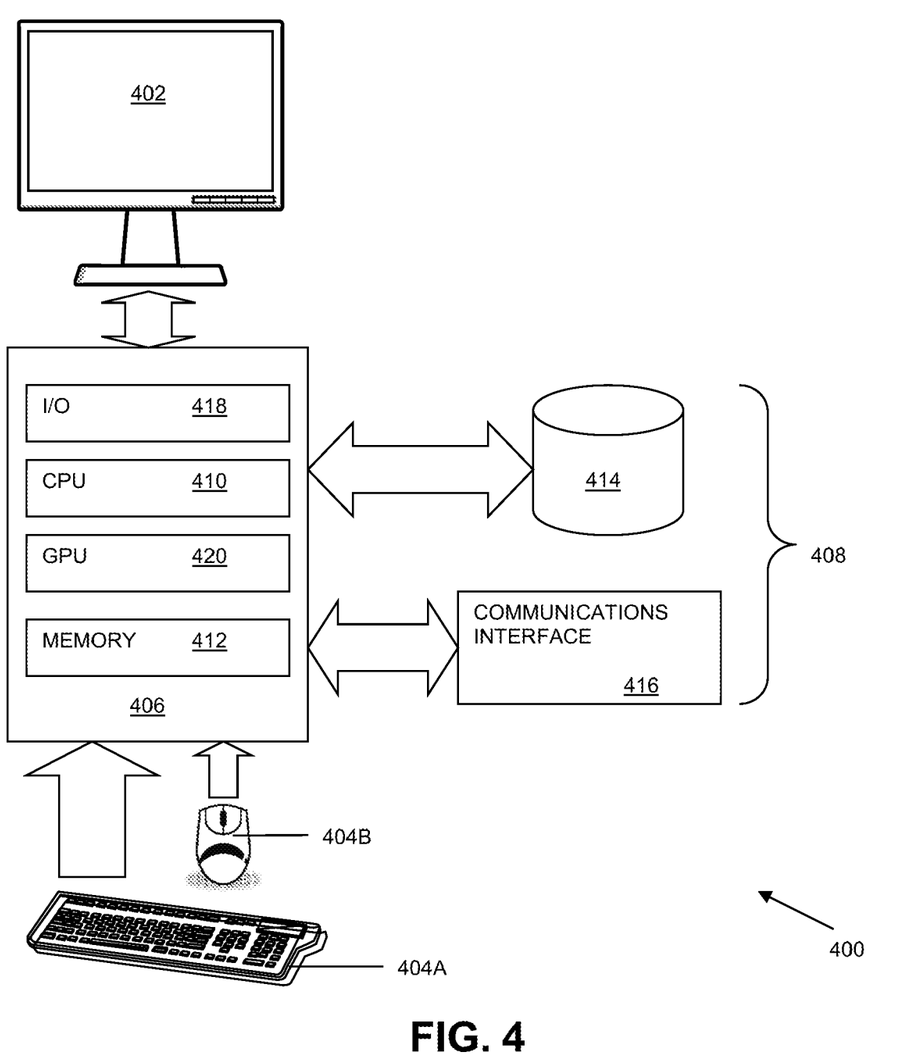
FIG. 4 is a block diagram showing an illustrative computer system in respect of which the technology herein described may be implemented.

An illustrative computer system in respect of which the technology herein described, for example the method, may be implemented is presented as a block diagram in FIG. 4. The illustrative computer system is denoted generally by reference numeral 400 and includes a display 402, input devices in the form of keyboard 404A and pointing device 404B, computer 406 and external devices 408. While pointing device 404B is depicted as a mouse, it will be appreciated that other types of pointing device, or a touch screen, may also be used. The computer 400 may implement aspects of the methods described herein, and may be, for example, the host computing platform 210.

The computer 406 may contain one or more processors or microprocessors, such as a central processing unit (CPU) 410. The CPU 410 performs arithmetic calculations and control functions to execute software stored in an internal memory 412, preferably random access memory (RAM) and/or read only memory (ROM), and possibly additional memory 414. The additional memory 414 may include, for example, mass memory storage, hard disk drives, optical disk drives (including CD and DVD drives), magnetic disk drives, magnetic tape drives (including LTO, DLT, DAT and DCC), flash drives, program cartridges and cartridge interfaces such as those found in video game devices, removable memory chips such as EPROM or PROM, emerging storage media, such as holographic storage, or similar storage media as known in the art. This additional memory 414 may be physically internal to the computer 406, or external as shown in FIG. 4, or both.

The computer system 400 may also include other similar means for allowing computer programs or other instructions to be loaded. Such means can include, for example, a communications interface 416 which allows software and data to be transferred between the computer system 400 and external systems and networks. Examples of communications interface 416 can include a modem, a network interface such as an Ethernet card, a wireless communication interface, or a serial or parallel communications port. Software and data transferred via communications interface 416 are in the form of signals which can be electronic, acoustic, electromagnetic, optical or other signals capable of being received by communications interface 416. Multiple interfaces, of course, can be provided on a single computer system 400.

Input and output to and from the computer 406 is administered by the input/output (I/O) interface 418. This I/O interface 418 administers control of the display 402, keyboard 404A, external devices 408 and other such components of the computer system 400. The computer 406 also includes a graphical processing unit (GPU) 420. The latter may also be used for computational purposes as an adjunct to, or instead of, the (CPU) 410, for mathematical calculations.

The various components of the computer system 400 are coupled to one another either directly or by coupling to suitable buses.

Figure 5:
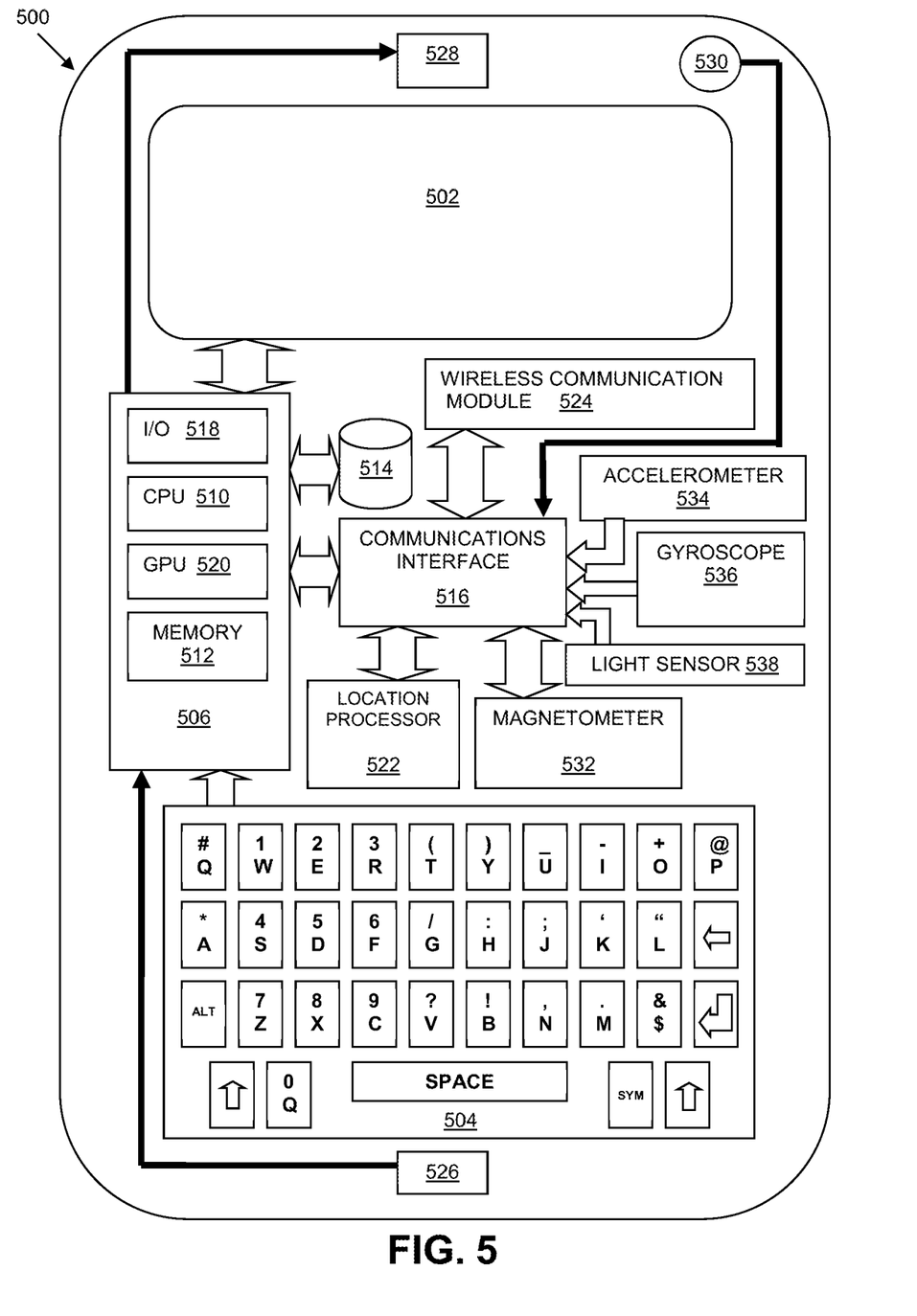
FIG. 5 is a block diagram showing an illustrative networked mobile wireless telecommunication computing device in the form of a smartphone.

FIG. 5 shows an illustrative networked mobile wireless telecommunication computing device in the form of a smartphone 500. The smartphone 500 may implement aspects of the methods described herein, or may be one of the computing devices 230 in FIG. 2, or be used, for example, by field personnel to receive sampling guidance based on the final sampling plan 122F, and may be coupled to a handheld qPCR machine to obtain analysis data. The smartphone 500 includes a display 502, an input device in the form of keyboard 504 and an onboard computer system 506. The display 502 may be a touchscreen display and thereby serve as an additional input device, or as an alternative to the keyboard 504. The onboard computer system 506 comprises a central processing unit (CPU) 510 having one or more processors or microprocessors for performing arithmetic calculations and control functions to execute software stored in an internal memory 512, preferably random access memory (RAM) and/or read only memory (ROM) is coupled to additional memory 514 which will typically comprise flash memory, which may be integrated into the smartphone 500 or may comprise a removable flash card, or both. The smartphone 500 also includes a communications interface 516 which allows software and data to be transferred between the smartphone 500 and external systems and networks. The communications interface 516 is coupled to one or more wireless communication modules 524, which will typically comprise a wireless radio for connecting to one or more of a cellular network, a wireless digital network or a Wi-Fi network. The communications interface 516 will also typically enable a wired connection of the smartphone 500 to an external computer system. A microphone 526 and speaker 528 are coupled to the onboard computer system 506 to support the telephone functions managed by the onboard computer system 506, and a location processor 522 (e.g. including GPS receiver hardware) may also be coupled to the communications interface 516 to support navigation operations by the onboard computer system 506. One or more cameras 530 (e.g. front-facing and/or rear facing cameras) may also be coupled to the onboard computer system 506, as may be one or more of a magnetometer 532, accelerometer 534, gyroscope 536 and light sensor 538. Input and output to and from the onboard computer system 506 is administered by the input/output (I/O) interface 518, which administers control of the display 502, keyboard 504, microphone 526, speaker 528, camera 530, magnetometer 532, accelerometer 534, gyroscope 536 and light sensor 538. The onboard computer system 506 may also include a separate graphical processing unit (GPU) 520. The various components are coupled to one another either directly or by coupling to suitable buses.

The term "computer system", "data processing system" and related terms, as used herein, is not limited to any particular type of computer system and encompasses servers, desktop computers, laptop computers, networked mobile wireless telecommunication computing devices such as smartphones, tablet computers, as well as other types of computer systems.

Thus, computer readable program code for implementing aspects of the technology described herein may be contained or stored in the memory 512 of the onboard computer system 506 of the smartphone 500 or the memory 412 of the computer 406, or on a computer usable or computer readable medium external to the onboard computer system 506 of the smartphone 500 or the computer 406, or on any combination thereof. In construing the claims, it is to be understood that where a computer-implemented method, a computer system or a computer program product is expressly recited in the claims, such computer-implementation, computer system or a computer program product, respectively, is essential to that claim.

The invention claimed is:

1. A computer implemented method for determining survey sampling parameters for environmental DNA (eDNA) detection, the method comprising:
   (a) receiving a species selection identifying at least one selected species;
   (b) receiving environmental specifications for an environment to be tested for presence of the at least one species;
   (c) receiving a current sampling plan, wherein the current sampling plan is generated using the environmental specifications and the species selection and comprises:
      total volume to be sampled;
      total number of samples;
      volume per sample; and
      sample locations;
   (d) receiving, for each of the selected species, a respective detectability prediction as to whether the respective selected species is detectable in the environment according to the current sampling plan, wherein the respective detectability prediction is generated using the environmental specifications, the species selection and the current sampling plan;
   (e) testing according to each respective detectability prediction, whether at least one respective selected species is undetectable according to the current sampling plan;
   (f) where, according to each respective detectability prediction, at least one respective selected species is undetectable according to the current sampling plan, iterating through step (c), step (d) and step (e), wherein each subsequent iteration of step (c) incorporates an increase in the total volume to be sampled, until the earlier of:
      (I) according to each respective detectability prediction, every respective selected species is detectable according to the current sampling plan; or
      (II) an iteration stop limit is reached; and
   (g) upon completion of step (e)(I), setting the then-current sampling plan as a final sampling plan;
   wherein:
      the respective detectability prediction as to whether the respective selected species is detectable in the environment according to the current sampling plan is generated using a detection prediction algorithm set;
      the current sampling plan is generated using a survey design algorithm set;
      and wherein the detection prediction algorithm set is different from the survey design algorithm set.

2. The method of claim 1, further comprising:
   before using the environmental specifications and the species selection to generate a first current sampling plan, providing the environmental specifications and the species selection to a filter; wherein the method terminates responsive to a determination by the filter that every selected species is undetectable in the environment.

3. The method of claim 2, wherein, for a particular one of the selected species, the filter determines that the selected species is undetectable in the environment because the selected species cannot be naturally present in the environment.

4. The method of claim 1, wherein the iteration stop limit is one of:
   a volume limit; and
   a number of iterations.

5. The method of claim 1, wherein, for a particular one of the selected species, the respective detectability prediction indicates that the respective species is undetectable according to the current sampling plan because the particular one of the species, if present in the environment, cannot be detected according to the current sampling plan.

6. The method of claim 1, wherein the environmental specifications comprise site type, study site surface area, study site perimeter, survey month, flow rate, water pH, water conductivity, water temperature, dissolved oxygen, turbidity, total suspended solids, total dissolved solids, presence of inhibitors, and eDNA detection results obtained from past surveys under given site data.

7. The method of claim 1, wherein each respective detectability prediction is derived from the environmental specifications and is further derived from a species-specific dataset for that species, the species-specific dataset comprising, for each species, the class of life, the species itself, average biomass, habitat preference, diet type, preferred water depth range, preferred temperature, spawning period, and detection limit.

8. The method of claim 1, wherein:
   the at least one species is at least one aquatic species;
   the environment is an aquatic environment; and
   the current sampling plan comprises filter pore size.

9. The method of claim 1, wherein the detection prediction algorithm set comprises at least two of Generalized Linear Model, Generalized Estimating Equation, Generalized Additive Model, Random Forest and Neural Network.

10. The method of claim 1, wherein, for a given selected species, the detectability prediction indicates that that selected species is detectable according to the current sampling plan where at least one of the detection prediction algorithms indicates that that selected species is detectable according to the current sampling plan.

11. A data processing system adapted for determining survey sampling parameters for environmental DNA (eDNA) detection, the system comprising:
   a host computing platform comprising one or more computers each with memory and at least one processor;
   a survey design interface configured to receive species selections each identifying at least one selected species and to receive environmental specifications for an environment to be tested for presence of the at least one species;
   a survey development iteration module comprising computer program instructions that when executing in the memory of the host computing platform, perform:
   (a) receiving a current sampling plan, wherein the current sampling plan is generated using the environmental specifications and the species selection and comprises:
      total volume to be sampled;
      total number of samples;
      volume per sample; and
      sample locations;
   (b) receiving, for each of the selected species, a respective detectability prediction as to whether the respective selected species is detectable in the environment according to the current sampling plan, wherein the respective detectability prediction is generated using the environmental specifications, the species selection and the current sampling plan;
   (c) testing according to each respective detectability prediction, whether at least one respective selected species is undetectable according to the current sampling plan;
   (d) where, according to each respective detectability prediction, at least one respective selected species is undetectable according to the current sampling plan, iterating through steps (a) step (b) and step (c) again, wherein each subsequent iteration of step (a) incorporates an increase in the total volume to be sampled, until the earlier of:
      (I) according to each respective detectability prediction, every respective selected species is detectable according to the current sampling plan; or
      (II) an iteration stop limit is reached; and
   (e) upon completion of step (d)(I), setting the then-current sampling plan as a final sampling plan;
   wherein:
      the respective detectability prediction as to whether the respective selected species is detectable in the environment according to the current sampling plan is generated using a detection prediction algorithm set;
      the current sampling plan is generated using a survey design algorithm set;
      and wherein the detection prediction algorithm set is different from the survey design algorithm set.

12. The data processing system of claim 11, wherein the computer program instructions when executing in the memory of the host computing platform, perform:
   before using the environmental specifications and the species selection to generate a first current sampling plan, providing the environmental specifications and the species selection to a filter; and
   responsive to a determination by the filter that every selected species is undetectable in the environment; declining to use the environmental specifications and the species selection to generate any sampling plan.

13. The data processing system of claim 12, wherein, for a particular one of the selected species, the filter determines that the selected species is undetectable in the environment because the selected species cannot be naturally present in the environment.

14. The data processing system of claim 12, wherein the iteration stop limit is one of:
   a volume limit; and
   a number of iterations.

15. The data processing system of claim 12, wherein, for a particular one of the selected species, the respective detectability prediction indicates that the respective species is undetectable according to the current sampling plan because the particular one of the species, if present in the environment, cannot be detected according to the current sampling plan.

16. The data processing system of claim 12, wherein the environmental specifications comprise site type, study site surface area, study site perimeter, survey month, flow rate, water pH, water conductivity, water temperature, dissolved oxygen, turbidity, total suspended solids, total dissolved solids, presence of inhibitors, and eDNA detection results obtained from past surveys under given site data.

17. The data processing system of claim 16, wherein each respective detectability prediction is derived from the environmental specifications and is further derived from a species-specific dataset for that species, the species-specific dataset comprising, for each species, the class of life, the species itself, average biomass, habitat preference, diet type, preferred water depth range, preferred temperature, spawning period, and detection limit.

18. The data processing system of claim 12, wherein:
   the at least one species is at least one aquatic species;
   the environment is an aquatic environment; and
   the current sampling plan comprises filter pore size.

19. The data processing system of claim 12, wherein the detection prediction algorithm set comprises at least two of Generalized Linear Model, Generalized Estimating Equation, Generalized Additive Model, Random Forest and Neural Network.

20. The data processing system of claim 12, wherein, for a given species, the detectability prediction indicates that that selected species is detectable according to the current sampling plan where at least one of the detection prediction algorithms indicates that that selected species is detectable according to the current sampling plan.

21. A computer program product for determining survey sampling parameters for environmental DNA (eDNA) detection, the computer program product including a tangible non-transitory computer readable storage medium having program instructions embodied therewith, the program instructions executable by a device to cause the device to perform a method including:
   (a) receiving a species selection identifying at least one selected species;
   (b) receiving environmental specifications for an environment to be tested for presence of the at least one species:
   (c) receiving a current sampling plan, wherein the current sampling plan is generated using the environmental specifications and the species selection and comprises:

total volume to be sampled;
total number of samples;
volume per sample; and
sample locations;
(d) receiving, for each of the selected species, a respective detectability prediction as to whether the respective selected species is detectable in the environment according to the current sampling plan, wherein the respective detectability prediction is generated using the environmental specifications, the species selection and the current sampling plan;
(e) testing according to each respective detectability prediction, whether at least one respective selected species is undetectable according to the current sampling plan;
(f) where, according to each respective detectability prediction, at least one respective selected species is undetectable according to the current sampling plan, iterating through step (c), step (d), and step (e) again, wherein each subsequent iteration of step (c) incorporates an increase in the total volume to be sampled, until the earlier of:
  (I) according to each respective detectability prediction, every respective selected species is detectable according to the current sampling plan; or
  (II) an iteration stop limit is reached; and
(g) upon completion of step (f)(I), setting the then-current sampling plan as a final sampling plan;
wherein:
  the respective detectability prediction as to whether the respective selected species is detectable in the environment according to the current sampling plan is generated using a detection prediction algorithm set;
  the current sampling plan is generated using a survey design algorithm set;
  and wherein the detection prediction algorithm set is different from the survey design algorithm set.

22. The computer program product of claim 21, wherein:
the instructions cause, before using the environmental specifications and the species selection to generate a first current sampling plan, the environmental specifications and the species selection to be provided to a filter; and
the method terminates responsive to a determination by the filter that every selected species is undetectable in the environment.

23. The computer program product of claim 22, wherein, for a particular one of the selected species, the filter determines that the selected species is undetectable in the environment because the selected species cannot be naturally present in the environment.

24. The computer program product of claim 23, wherein the iteration stop limit is one of:
a volume limit; and
a number of iterations.

25. The computer program product of claim 23, wherein, for a particular one of the selected species, the respective detectability prediction indicates that the respective species is undetectable according to the current sampling plan because the particular one of the species, if present in the environment, cannot be detected according to the current sampling plan.

26. The computer program product of claim 23, wherein the environmental specifications comprise site type, study site surface area, study site perimeter, survey month, flow rate, water pH, water conductivity, water temperature, dissolved oxygen, turbidity, total suspended solids, total dissolved solids, presence of inhibitors, and eDNA detection results obtained from past surveys under given site data.

27. The computer program product of claim 26, wherein each respective detectability prediction is derived from the environmental specifications and is further derived from a species-specific dataset for that species, the species-specific dataset comprising, for each species, the class of life, the species itself, average biomass, habitat preference, diet type, preferred water depth range, preferred temperature, spawning period, and detection limit.

28. The computer program product of claim 23, wherein:
the at least one species is at least one aquatic species;
the environment is an aquatic environment; and
the current sampling plan comprises filter pore size.

29. The computer program product of claim 23, wherein the detection prediction algorithm set comprises at least two of Generalized Linear Model, Generalized Estimating Equation, Generalized Additive Model, Random Forest and Neural Network.

30. The computer program product of claim 23, wherein, the detectability prediction indicates that that selected species is detectable according to the current sampling plan where at least one of the detection prediction algorithms indicates that that selected species is detectable according to the current sampling plan.

* * * * *